US00PP33792P2

(12) United States Plant Patent
Van Swieten

(10) Patent No.: US PP33,792 P2
(45) Date of Patent: Dec. 28, 2021

(54) ***PHALAENOPSIS* ORCHID PLANT NAMED 'PHA1437158'**

(50) Latin Name: ***Phalaenopsis* hybrid**
Varietal Denomination: PHA1437158

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,547

(22) Filed: Aug. 11, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA1437158', particularly characterized by having large white flowers with a pure white and extra-large lip, flowers that are flat in lateral view, dorsal sepals with an incurving curvature of the longitudinal axis, and is propagated by meristem tissue culture, is disclosed.

3 Drawing Sheets

Genus and species: *Phalaenopsis* hybrid.
Variety denomination: 'PHA1437158'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1437158'.

The new *Phalaenopsis* plant is a product of a planned breeding program conducted by the inventor in Bleiswijk, the Netherlands. The objective of this breeding program was to create a new *Phalaenopsis* plant with numerous attractive large white flowers with a white and extra-large lip, suitable for potted plant production.

The new *Phalaenopsis* plant 'PHA1437158' is a result of cross-pollination made by the inventor in September 2012 in Bleiswijk, the Netherlands, of the proprietary female, or seed parent, *Phalaenopsis* hybrid '01-4326' (unpatented) with the proprietary male, or pollen parent, *Phalaenopsis* hybrid 'PHALGOWIJ' (U.S. Plant Pat. No. 30,300).

The new *Phalaenopsis* was selected by the inventor as a single plant within the progeny of the stated cross-pollination in a controlled greenhouse in Bleiswijk, the Netherlands, in May 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2293), by Applicant who obtained the subject matter disclosed directly from the inventor. 'PHA1437158' has not been made publicly available or sold anywhere in the world prior to the effective filing date of this application with the exception of sales or disclosures made one year or less before the effective filing date of this claimed invention by Applicant who obtained 'PHA1437158' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1437158' as a new and distinct variety of *Phalaenopsis* plant:

1) Large white flowers with a white and extra-large lip;
2) Lip is pure white;
3) Flower shape in lateral view is flat; and
4) Curvature of longitudinal axis of dorsal sepal is incurving.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in May 2021. Colors in the photographs may differ from the color values cited in the detailed botanical description, which accurately describe the actual colors of the new variety.

DESCRIPTION OF THE NEW VARIETY

Figure 1:
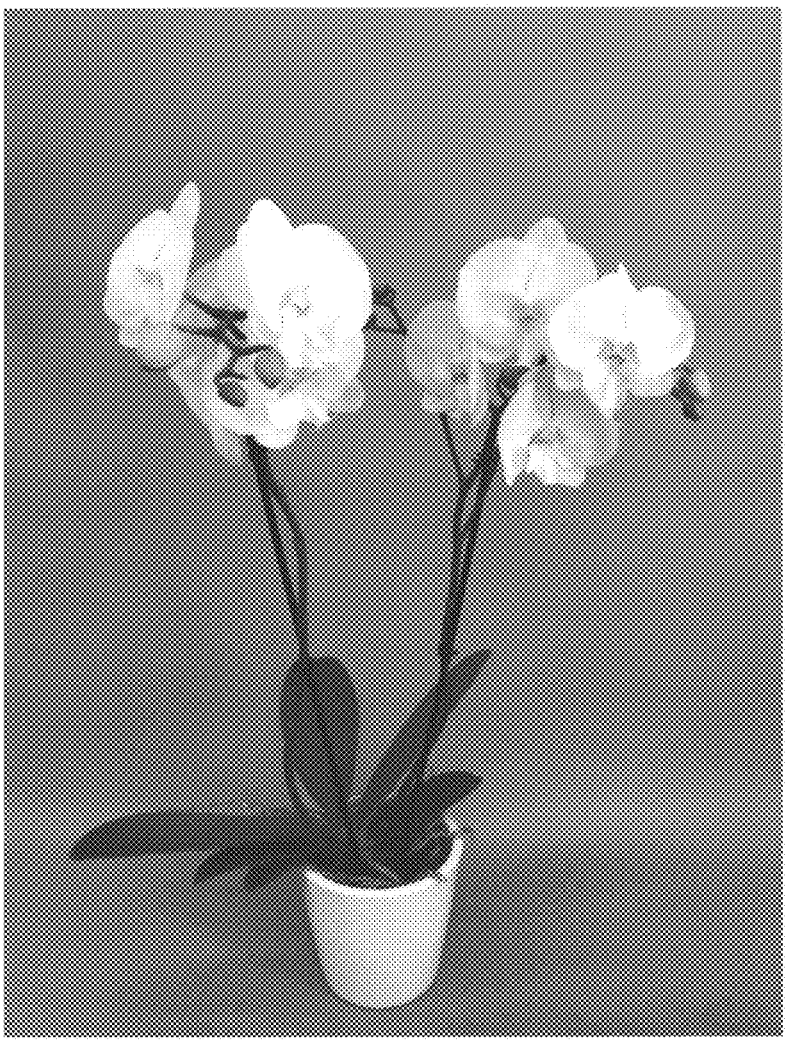
FIG. 1 shows the overall plant habit, including blooms, buds, and foliage of 'PHA1437158'.
Figure 2:
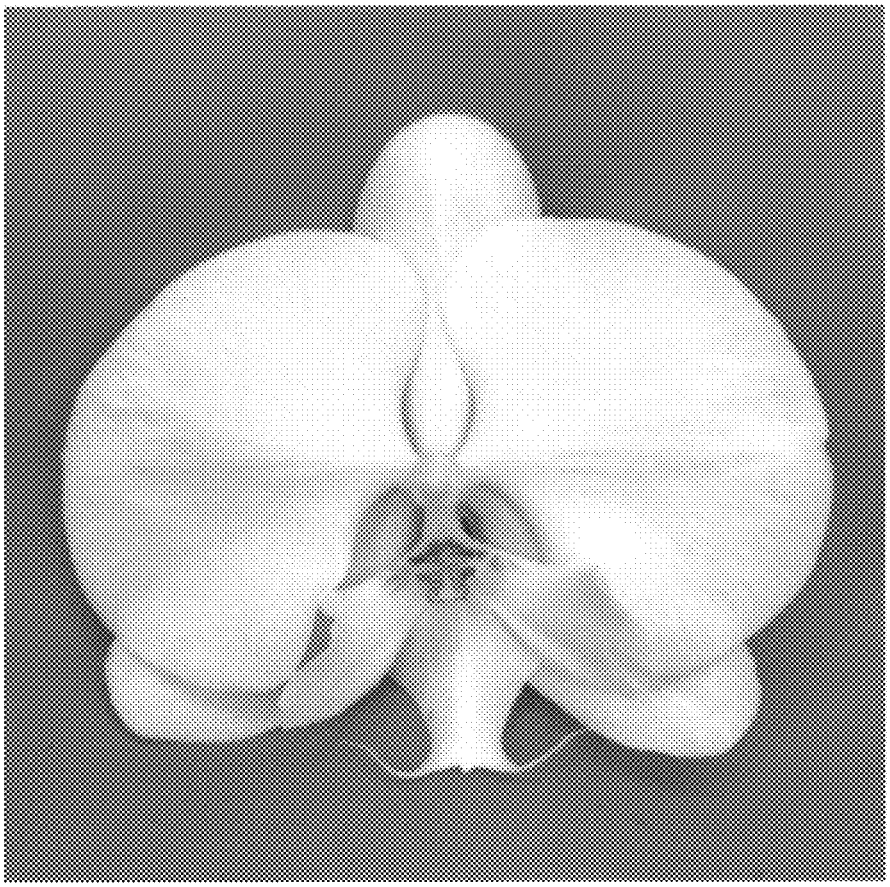
FIG. 2 shows a close-up of a flower of 'PHA1437158'.
Figure 3:
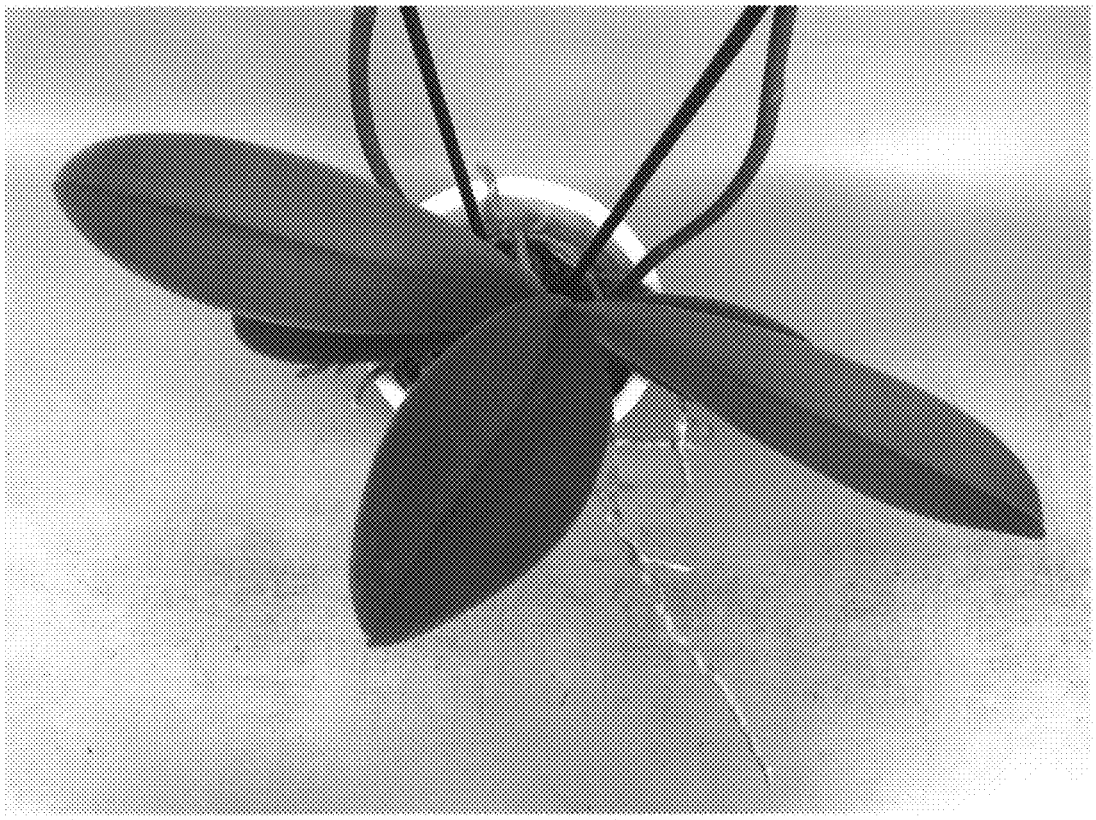
FIG. 3 shows an overhead view of the leaves of 'PHA1437158'.

The following detailed description sets forth the distinctive characteristics of 'PHA1437158'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in May 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1437158'.

Parentage:

*Female parent*.—*Phalaenopsis* cultivar '01-4326' (unpatented).

*Male parent*.—*Phalaenopsis* cultivar 'PHALGOWIJ' (U.S. Plant Pat. No. 30,300).

Propagation:

*Type*.—Meristem tissue culture.

Roots:

*Root description*.—Greyed-green (a color in between RHS 190B and RHS 190C) colored roots with branching lateral roots having yellow-green (RHS 145A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 59.0 cm to 64.0 cm.

*Width* (*measured from leaf tips*).—About 37.0 cm to 40.0 cm.

*Vigor*.—Moderate.

Leaves:

*Mature leaves*.—Quantity per plant: 6 to 8 leaves are produced before flowering. Length (fully expanded): 21.0 cm to 24.0 cm. Width: 6.5 cm to 7.5 cm. Shape: Obovate. Base shape: Moderately to very elongated. Apex: Acute unequal. Leaf blade angle with the petiole (measured from the horizontal position): Between 15 degrees and 30 degrees. Leaf margin: Entire. Color: Upper surface: RHS 146A. Lower surface: RHS 146B. Texture (both upper and lower surfaces): Smooth. Thickness: 2.1 mm to 2.4 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—6 to 8.

*Length*.—59.0 cm to 64.0 cm.

*Diameter*.—6.0 mm to 7.0 mm.

*Strength*.—Strong.

*Aspect*.—Upright to slightly pendent.

*Texture*.—Smooth.

*Color*.—Yellow-green (a color in between RHS 144A and RHS 146B).

*Internode length*.—3.0 cm to 4.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 270.0 mm to 290.0 mm.

*Flowering time*.—First flowers can be expected 10 to 11 months after planting in a 12-cm pot.

*Flower*.—Height: 98.0 mm to 103.0 mm. Diameter: 105.0 mm to 110.0 mm. Depth of lip: About 3.0 mm.

*Flower shape*.—Flat.

*Flower longevity*.—On the plant: 20 to 22 weeks.

*Fragrance*.—Absent.

*Flower bud*.—Average size: Medium to large. Length: 23.0 mm to 25.0 mm. Width: 18.0 mm to 20.0 mm. Shape: Egg shaped. Color: Yellow-green (a color in between RHS 144C and RHS N144D).

*Petals*.—Arrangement: Open/free. Shape: Semi-circular. Apex: Slightly emarginated asymmetric. Margin: Moderately undulated. Length (from base to tip): 47.0 mm to 49.0 mm. Width: 66.0 mm to 68.0 mm. Position of the broadest part of the petal: At the base. Color (when fully opened): Upper surface: Basic color: White (RHS NN155C). Over color: Absent. Lower surface: Basic color: White (RHS NN155C). Over color: Absent. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 52.0 mm to 54.0 mm. Width: 33.0 mm to 35.0 mm. Color (when fully opened): Upper surface: Basic color: White (RHS NN155C). Over color: Absent. Lower surface: Basic color: White (RHS NN155C). Over color: Light yellow-green (RHS 145D). Number of spots and stripes on the dorsal sepals (upper surface): None. Color of spots and stripes on the dorsal sepals (upper surface): Not applicable. Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 52.0 mm to 54.0 mm. Width: 30.0 mm to 32.0 mm. Color (when fully opened): Upper surface: Basic color: White (RHS NN155C). Over color: Absent. Lower surface: Basic color: White (RHS NN155C). Over color: Light yellow-green (RHS 145C). Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Overall shape: 3-lobed with callus at central junction of the lateral lobes and base of apical lobe. The apical lobe is terminated by 2 whiskers. Lateral lobes and apical lobe are connected.

*Lateral lobe*.—Margin: Moderately undulated. Length: 27.0 mm to 29.0 mm. Width: 23.0 mm to 25.0 mm. Color: Upper surface: White (RHS NN155C) with a touch of light yellow-green (RHS 145C); few purplish-pink spots (RHS N78C) and light reddish-purple stripes (RHS N78D) at the base Lower surface: White (RHS NN155C). Number of spots and stripes on the lateral lobe (upper surface): Few spots; few stripes at the base. Color of spots and stripes on the lateral lobe (upper surface): Spots (RHS N78C); stripes (RHS N78D). Density of netting of the lateral lobe (upper surface): None. Color of the netting (upper surface): Not applicable.

*Apical lobe*.—Shape: Triangular. Margin: Entire. Length: 24.0 mm to 26.0 mm. Width: 28.0 mm to 30.0 mm. Color: Upper surface: White (RHS NN155C). Lower surface: White (RHS NN155C). Number of spots and stripes on the apical lobe (upper surface): None. Color of spots and stripes on the apical lobe (upper surface): Not applicable. Density of netting of the apical lobe (upper surface): None. Color of the netting (upper surface): Not applicable. Whiskers: Present. Length of whiskers: 16.0 mm to 18.0 mm. Color of whiskers: White (RHS NN155C). Pubescence on the lip: Absent.

*Callus*.—Average size: Large. Height: 9.0 mm to 10.0 mm. Length: 7.0 mm to 8.0 mm. Width: 4.0 mm to 5.0 mm. Color: Light yellow-green (RHS 157B) at the base and yellow-green (RHS 154C) on sides; dotted (RHS 72A).

Reproductive organs:

*Column*.—Length: 8.0 mm to 10.0 mm. Diameter: 5.0 mm to 6.0 mm. Color: White (RHS NN155C).

*Pollinia*.—Quantity: 2. Diameter: 0.9 mm to 1.1 mm. Color: Orange (RHS 25A).

*Ovary*.—Length: 18.0 mm to 20.0 mm. Diameter: 2.8 mm to 3.2 mm.

*Pedicel*.—Length: 40.0 mm to 42.0 mm. Diameter: 3.4 mm to 3.7 mm. Color: Light yellow-green (RHS 145B) at the base; lighter yellow-green (RHS 145D) toward flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1437158' differs from the female parent plant '01-4326' (unpatented) in that 'PHA1437158' has dorsal sepals with a light yellow-green overcolor on the lower surface and lighter green (RHS 146A) leaves, whereas '01-4326' has dorsal sepals with a light purple and light yellow-green overcolor on the lower surface and darker green (RHS 147A) leaves.

'PHA1437158' differs from the male parent plant 'PHALGOWIJ' (U.S. Plant Pat. No. 30,300) in that 'PHA1437158' has apical lobes that are white at the base and an extra-large lip type, whereas 'PHALGOWIJ' has apical lobes that are light yellow-green at the base and a normal lip type. Additionally, 'PHA1437158' has larger flowers than 'PHALGOWIJ'.

'PHA1437158' is most similar to the commercial *Phalaenopsis* plants named 'PHALGASEOT' (U.S. Plant Pat. No. 31,212) and 'PHALGRUSEI' (U.S. Plant Pat. No. 33,146). 'PHA1437158' differs from the commercial variety 'PHALGASEOT' in that 'PHA1437158' has obtuse dorsal sepal apexes, whereas 'PHALGASEOT' has slightly emarginated dorsal sepal apexes. Additionally, 'PHA1437158' has wider petals and longer whiskers than 'PHALGASEOT'.

'PHA1437158' differs from the commercial variety 'PHALGRUSEI' in that 'PHA1437158' has obtuse dorsal sepal apexes and flowers with an even pattern, whereas 'PHALGRUSEI' has slightly obtuse to rounded dorsal sepal apexes and flowers with a striped pattern. Additionally, 'PHA1437158' has wider petals and longer whiskers than 'PHALGRUSEI'.

I claim:

1. A new and distinct variety of *Phalaenopsis* plant named 'PHA1437158', substantially as described and illustrated herein.

* * * * *